United States Patent [19]
Bolze

[11] Patent Number: 5,954,269
[45] Date of Patent: Sep. 21, 1999

[54] INSTALLATION FOR AUTOMATICALLY PURIFYING PREMISES SUCH AS TOILETS

[75] Inventor: Bernard Bolze, La Croix en Touraine, France

[73] Assignee: Sanitaire Equipement, Tours, France

[21] Appl. No.: 08/825,094

[22] Filed: Mar. 27, 1997

[30] Foreign Application Priority Data

Apr. 1, 1996 [FR] France .................................. 96 04049

[51] Int. Cl.⁶ .................................................. E03D 9/00
[52] U.S. Cl. ............................. 239/70; 239/127; 4/228.1
[58] Field of Search .................... 239/124, 127, 239/70; 4/228.1; 137/674

[56] References Cited

U.S. PATENT DOCUMENTS

| | | | |
|---|---|---|---|
| 4,061,271 | 12/1977 | Kimbrough | 239/127 X |
| 4,324,294 | 4/1982 | McLoughlin et al. | 239/127 X |
| 4,387,850 | 6/1983 | Gerber | 239/124 |
| 5,397,054 | 3/1995 | Ziegs | 239/124 X |
| 5,520,333 | 5/1996 | Tofte | 239/127 X |
| 5,571,259 | 11/1996 | Takasu | 239/127 X |

FOREIGN PATENT DOCUMENTS

| | | |
|---|---|---|
| 0 485 682 A1 | 5/1992 | European Pat. Off. . |
| 0 559 268 A1 | 9/1993 | European Pat. Off. . |
| 2302105 | 9/1976 | France . |

OTHER PUBLICATIONS

WO 90/12600, published Nov. 1, 1990.

Primary Examiner—Kevin Weldon
Attorney, Agent, or Firm—Fisher, Christen & Sabol

[57] ABSTRACT

The present invention relates to an installation for automatically purifying one or more enclosures located in one or more premises, such as toilets, comprising:
- a supply module comprising a control panel and a reservoir of liquid purifying product;
- at least one module for spraying the purifying product, comprising an electrovalve and a spray;
- each spray module being connected to the supply module via a single pipe;

characterized in that it comprises means for placing said product under pressure, solely in said pipe, the pressure being substantially greater than atmospheric pressure.

8 Claims, 3 Drawing Sheets

INSTALLATION FOR AUTOMATICALLY PURIFYING PREMISES SUCH AS TOILETS

FIELD OF THE INVENTION

The present invention relates to an installation for automatically purifying one or more enclosures located in one or more premises, equipped with sanitary toilets, and in particular for collectivities.

BACKGROUND OF THE INVENTION

EP 485.682 discloses an automatic installation composed of a central apparatus comprising a control panel, a reservoir of liquid purifying product provided with a compression device and means for spraying a liquid purifying product. The reservoir is connected to the spray means via a single tube. The purifying product contained in the reservoir and in said tube is placed under slight overpressure in order to be projected into the enclosure as soon as the spray means are opened. Now, the pressurization of the product contained in the resrvoir eliminates any possibility of removal of the latter and renders resupply thereof difficult.

Pressure by-pass means are then necessary at the level of the reservoir to allow it to be filled via a specific pipe or to intervene on the installation for maintenance thereof or for a particular repair. This known installation is open to improvement.

In this context, the present invention proposes a simplified installation allowing easy access to the different elements, providing a removable reservoir and increasing the efficiency of spraying of the product.

SUMMARY OF THE INVENTION

To that end, according to the invention, the present invention relates to an installation for automatically purifying one or more enclosures located in one or more premises, such as toilets, comprising:

a supply module comprising a control panel and a reservoir of liquid purifying product;

at least one module for spraying the purifying product, comprising an electrovalve and a spray;

each spray module being connected to the supply module via a single pipe;

characterized in that it comprises means for placing said product under pressure, solely in said pipe, the pressure being substantially greater than atmospheric pressure.

The installation advantageously comprises means for actuating the supply module and the spray module, adapted to allow separate and independent operation thereof.

The pressurization means comprise a low-inertia pump.

The supply module comprises a filter mounted upside down so as to create an air bubble therein.

The reservoir is preferably removable.

According to an advantageous embodiment, the installation comprises bleed means constituted by an electrovalve and an additional conduit disposed between the pipe and the reservoir.

The supply module comprises a timer capable of automatically stopping pressurization, after a pre-regulated time, in the event of break of a pipe, or if the reservoir is empty.

The spray module comprises an electronic card for managing operation thereof, said card comprising deletable elements memorizing data such as the presence of a user in said premises, the triggering off and interruption of spraying, the duration of spraying, the quantity of liquid sprayed.

According to one embodiment, operation of the spray module is triggered off by the actuation of a mechanical member such as a lock.

The liquid is taken to a pressure included between 3 and 10 bars, and preferably about 4.5 bars.

BRIEF DESCRIPTION OF THE DRAWINGS

The invention will be more readily understood on reading the following description with reference to the accompanying drawings, in which.

DESCRIPTION OF PREFERRED EMBODIMENT

Figure 1:
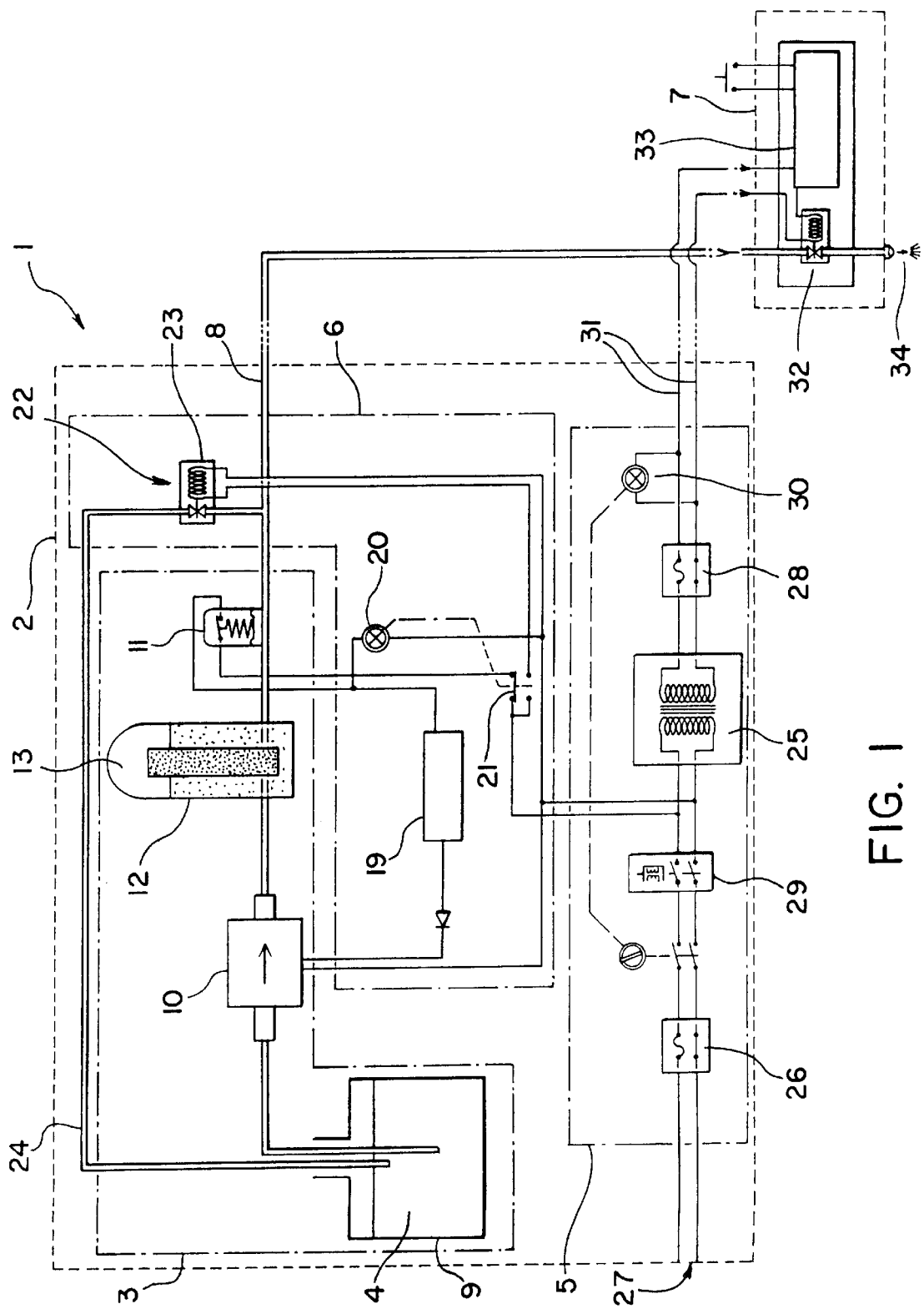
FIG. 1 shows a block diagram of the installation according to the invention including a supply module and a spray module.

Referring now to the drawings, FIG. 1 shows an installation 1 for automatically purifying one or more closed enclosures, such as toilets, which comprises:

a supply module 2 intended to manage the device 3 supplying purifying product 4 and the device 5 supplying electricity to the installation, as well as the safety devices 6 intended to protect the latter and allow easy and rapid intervention in the event of breakdown;

at least one spray module 7 intended to project the liquid purifying product in the enclosure; one spray module 7 is provided per enclosure, in the hypothesis of premises for sanitary use, provided with a pluraltiy of enclosures or sanitary units;

a single pipe 8 connecting the supply module 2 and the spray module(s) 7; only one spray module 7 has been shown in FIG. 1 for reasons of convenience. Where several spray modules are provided, they are disposed in series and connected to the supply module 2 by the single pipe 8 which, in that case, branches out at its end towards the spray modules.

Figure 2:
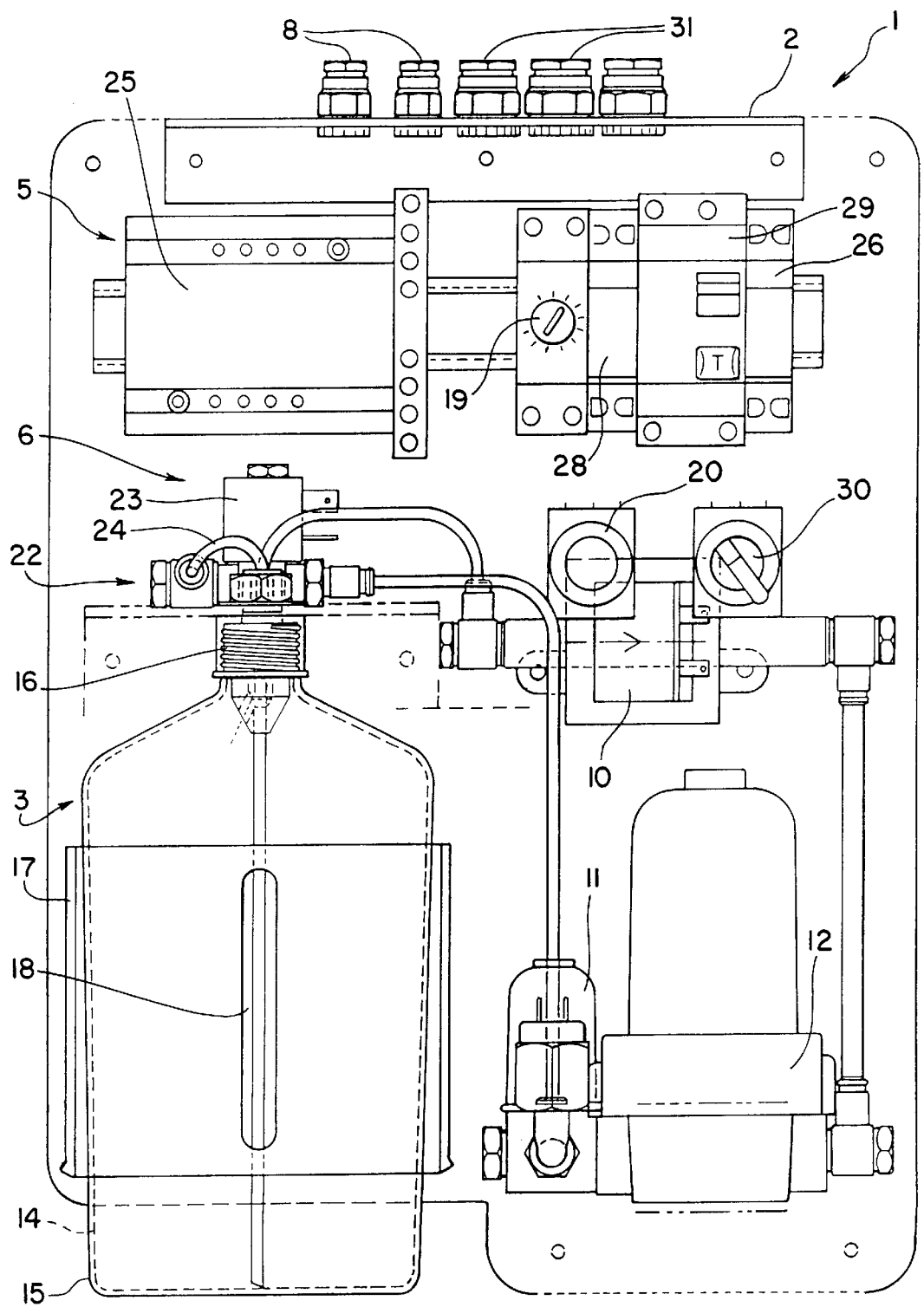
FIG. 2 shows a detailed front elevational view of the supply module of FIG. 1.
Figure 3:
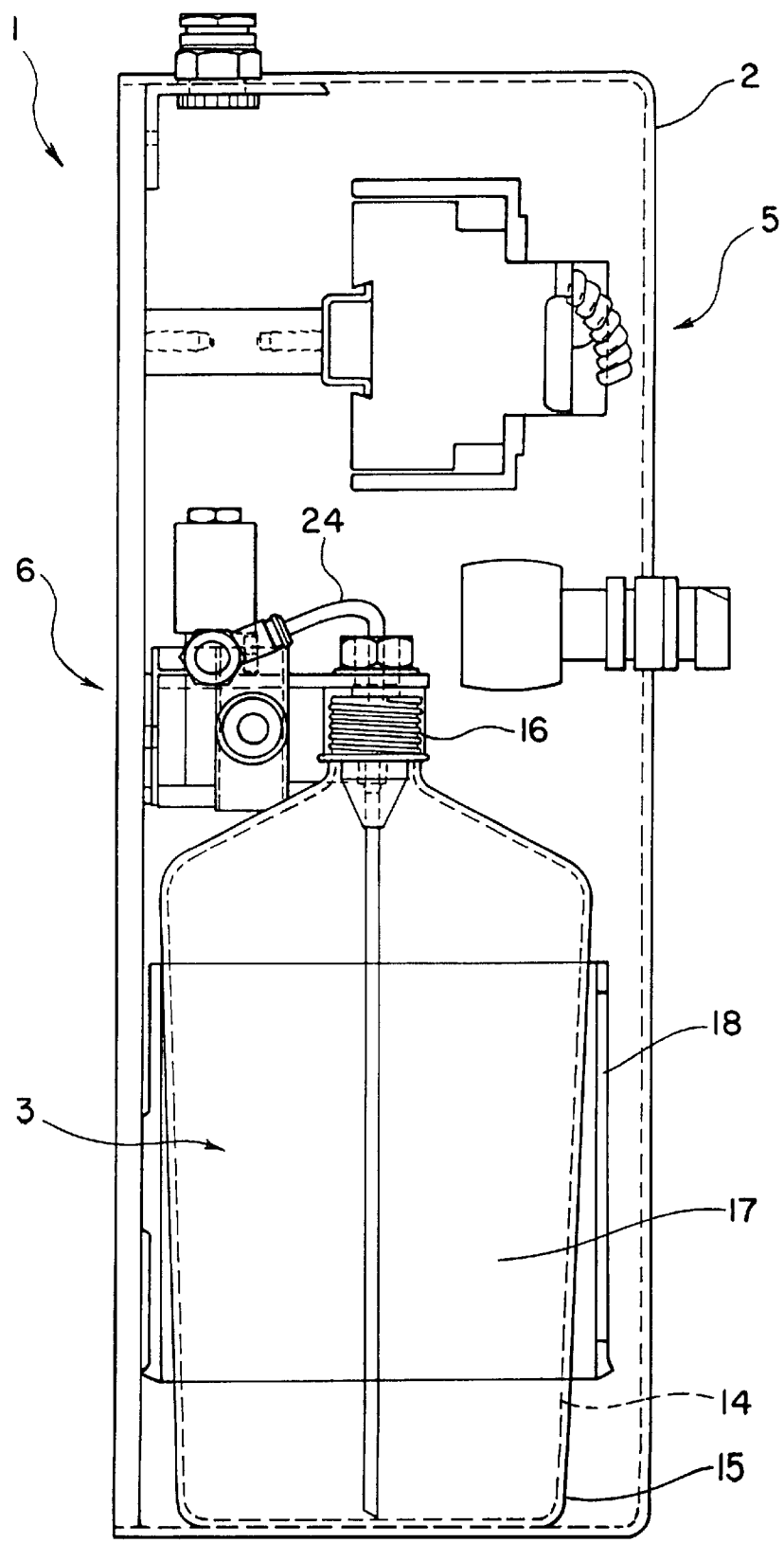
FIG. 3 shows a detailed side view of FIG. 2.

As shown in FIGS. 1 to 3, the supply module 2 comprises three parts:

a device 3 for supplying purifying product, a device 5 for supplying electricity, and a safety device 6.

The device 3 for supplying purifying product 4 comprises:

a reservoir 9 containing the purifying product, and a pump 10 capable of sucking the product 4 from the reservoir 9 and introducing it into the pipe 8 under a pressure greater than atmospheric pressure.

The purifying product 4 is placed under a pressure of about 3 to 10 bars, and preferably of the order of 4.5 bars. The pump 10 is of the low inertia type and is therefore capable of reacting in a time of about ⅕₀th of a second. For example, an electromagnetic low-inertia pump will suit. The pressure is regulated by a pressure controller 11.

A filter 12 is mounted upside down at the outlet of the pump 10. An air bubble 13 is thus created in its upper part, dampening the possible sudden rises in pressure. The filter 12 performs the role of a hydropneumatic accumulator. As soon as a spray is effected, the pump 10 makes it possible, if necessary, to compensate the loss of pressure in the installation. The purifying product contained in the reservoir 9 is at no time placed under pressure; only the pipe 8 is placed under pressure. In this way, the volume of purifying product under pressure is low, which limits the risk of fire in the event of accidental break of the pipe.

The reservoir 9 is preferably removable and, as shown in FIG. 2, is in the form of a container 14 of thermoplastic material such as polyethylene. An envelope 15 is adapted to receive the container 14. A screw-type fixing system 16 is provided at the upper end of the envelope 15. In this way, the container 14 provided with the envelope 15 can be easily screwed on corresponding means of the supply module 2.

The container 14 presents at its upper end (i.e. towards the fixing system 16) a diameter greater than the diameter of the container at its lower end. For example, the container presents a diameter of 12 cm at its upper end and of 11 cm at its lower end. The difference in diameter varies by about 50 mm to 2 cm.

A sheath 17 is fixed on the supply module 2 and presents a longitudinal slot 18 included in the plane tangential to the sheath and parallel to the plane of the module on which all the constituent parts thereof are placed. The function of the slot 18 is to allow a direct reading of the water level in the reservoir 9, i.e. in the container 14 in the example described.

The supply module 2 is for example in the form of a parallelepipedic box with the following dimensions:

the length of the box is included between 20 and 50 cm and is preferably 30.6 cm;

the height is included between 20 and 80 cm and is preferably 43.6 cm; and the depth is about 10 to 30 cm and preferably 15.4 cm.

The safety device 6 comprises:

a timing system 19 disposed in series with the pump 10 and connected to the pressure controller 11;

a visual alarm 20 connected to the output of the timing system 19 and to the pump 10;

a mechanical member 21 (circuit breaker) of the push button type connected, on the one hand, to the device 5 supplying electricity and, on the other hand, to the pressure controller 11;

a bleed system 22 electrically connected to the pump 10 and to the push button 21.

When the reservoir is empty or one of the pipes of the installation is broken, the pressure decreases until it reaches atmospheric pressure. The device 6 detects this at the pressure controller 11 and triggers off the timing system 19.

After a time pre-regulated by the user at the level of system 19, between about 10 and 50 seconds depending on the size of the installation, the functioning of the pump is automatically interrupted. The visual alarm 20 lights up to warn the user of a possible incident or that the reservoir is empty. The pump 10 remains inactive and the visual indicator 20 remains lit up as long as the user has not actuated the push button 21.

The bleed system 22 is constituted for example by a bleed electrovalve 23 making it possible to suck in the air or the purifying product from the pipe 8 and to introduce it in a bleed conduit 24 opening out into the reservoir 9.

The function of the bleed system 22 is, in particular, to reduce the pressure of the liquid in the installation to atmospheric pressure in order to allow the user to intervene thereon. It is also intended to evacuate the excess air when the installation is started up.

The bleed system 22 may be actuated by means of the push button 21.

The device 5 for electrical supply comprises:

a transformer 25 intended to supply the spray module(s) 7;

fuses 26 at the connection to the mains 27;

fuses 28 at the output of the transformer 25;

a differential circuit breaker 29 possibly added to reinforce safety of the device 5;

a telltale 30 indicating operation disposed at the output of the transformer 25.

The electrical supply device 5 is connected to the mains 27 (220 V–50 Hz) and is connected either to the bleed system 22 if the push button 21 is actuated, otherwise to the pressure controller 11.

The different component parts of the supply device 3 and of the safety device 6 are supplied at 220 volts. On the other hand, in order to limit the risks of electrocution, the spray module(s) is/are supplied at 24 volts. To that end, the transformer 25 is provided to supply the spray module(s) at 24 volts (A.C. or D.C.) from the current delivered by the mains 27 (220 V).

The operation telltale 30 indicates whether the spray module(s) is/are supplied.

The alarm indicator 20 and the operation telltale 30 present different colours. For example, indicator 20 is yellow, 30 is green.

Accumulator batteries (not shown) may be incorporated in the supply device 5 to ensure emergency supply in the event of breakdown or interruption of the mains.

Each spray module 7 is supplied with purifying product via the pipe 8, and electrically supplied at 24 volts by the device 5 of the supply module 2 via electric connection cables 31.

As shown in FIG. 1, the spray module 7 comprises an electrovalve 32 whose functioning is managed by an electronic card 33.

A nozzle 34 allows the product 4 to be injected into the enclosure; it may be integrated in the electrovalve 32. The card 33 makes it possible to activate spray when a condition is fulfilled, such as the presence of the user in the enclosure or the opening of the lock when the user leaves. Delay times may be regulated. In this way, a period of four seconds may for example be provided between the opening of the lock and the spraying, to allow the user to leave the enclosure before spraying begins.

The card 33 is also adapted to interrupt spraying after a determined, pre-regulated time by means of a potentiometer. The duration of spraying is a function of the quantity of purifying product 4 necessary to disinfect the enclosure correctly and entirely. For a pressure of 4.5 bars, the speed of spraying is substantially constant and about 1.5 ml per second for example.

Depending on the dimensions of the enclosures, the dimensions and power of each spray module 7 differ. The dimensions and power of the supply module 2 are selected as a function of the number and/or power of the spray modules, as well as of the configuration of the premises and the place allocated to each module.

The functioning of the supply module 2 and of the spray module(s) 7 is completely separate and independent, which makes it possible to reduce the number of connections between modules and to simplify the structure thereof.

Furthermore, the supply and spray modules may be installed easily, without being hindered by particular structures of premises which are for example remote from one another.

What is claimed is:

1. An installation for automatically purifying one or more toilets, comprising:

a supply module (2) comprising:

a device (3) for supplying purifying product with a reservoir (9) of liquid purifying product, a pump (10) capable of sucking the product from the reservoir (9), and a pressure controller (11), and a device (5) for supplying electricity, at least one module (7) for spraying the purifying product comprising an electrovalve and a spray nozzle, characterized in that each at least one spray nozzle (7) is connected to the supply module (2) via a single pipe (8), and the supply module (2) comprises also a safety device (6) comprising:

a timing system (19) disposed in series with the pump (10) and connected to the pressure controller (11), which automatically stops pressurization, after a pre-regulated time, in the event of break of a pipe or if the reservoir is empty;

a visual alarm (20) connected to the output of the timing system (19) and to the pump (10); and a mechanical member (21) of the push button type connected to the device (5) supplying electricity and connected to the pressure controller (11).

2. The installation of claim 1, wherein the installation further comprises means for actuating the supply module and the spray module, which are adapted to allow separate, independent functioning thereof.

3. The installation of claim 1, wherein the installation further comprises a filter (12) mounted upside down so as to create an air bubble therein.

4. The installation of claim 1, wherein the reservoir is removable.

5. The installation of claim 1, wherein the spray module comprises an electronic card for managing functioning thereof, said card comprising cancelable elements capable of memorizing data such as the presence of a user in the enclosure, the triggering off and interruption of the spraying, the duration of spraying, the quantity of liquid sprayed.

6. The installation of claim 4, wherein an envelope (15) is adapted to receive the reservoir (9) in the form of a container (14).

7. The installation of claim 6, wherein the container (14) presents at its upper end a diameter greater than the diameter of the container at its lower end.

8. The installation of claim 1, wherein a sheath (17) is fixed on the supply module (2).

* * * * *